(12) United States Patent
Schmieding

(10) Patent No.: US 7,548,865 B2
(45) Date of Patent: Jun. 16, 2009

(54) METHOD OF SELLING PROCEDURE SPECIFIC ALLOGRAFTS AND ASSOCIATED INSTRUMENTATION

(75) Inventor: Reinhold Schmieding, Naples, FL (US)

(73) Assignee: Arthrex, Inc., Naples, FL (US)

( * ) Notice: Subject to any disclaimer, the term of this patent is extended or adjusted under 35 U.S.C. 154(b) by 1133 days.

(21) Appl. No.: 09/981,752

(22) Filed: Oct. 19, 2001

(65) Prior Publication Data

US 2002/0049613 A1    Apr. 25, 2002

Related U.S. Application Data

(60) Provisional application No. 60/241,764, filed on Oct. 20, 2000.

(51) Int. Cl.
  *G06Q 50/00* (2006.01)
(52) U.S. Cl. .................. 705/2; 705/3; 600/300
(58) Field of Classification Search ............ 705/2, 705/3; 600/300
  See application file for complete search history.

(56) References Cited

U.S. PATENT DOCUMENTS

| | | | | |
|---|---|---|---|---|
| 4,852,554 A | * | 8/1989 | Alten ................. | 128/897 |
| 5,040,677 A | * | 8/1991 | Tubo et al. ........... | 206/440 |
| 5,682,886 A | * | 11/1997 | Delp et al. ........... | 600/407 |
| 5,732,401 A | * | 3/1998 | Conway .............. | 705/29 |
| 5,791,907 A | * | 8/1998 | Ramshaw et al. ....... | 434/262 |
| 5,919,196 A | * | 7/1999 | Bobic et al. .......... | 606/86 |
| 6,089,867 A | * | 7/2000 | Filho ................. | 433/215 |
| 6,425,920 B1 | * | 7/2002 | Hamada ............... | 623/17.16 |
| 6,447,545 B1 | * | 9/2002 | Bagby ................ | 623/17.16 |
| 6,497,726 B1 | * | 12/2002 | Carter et al. .......... | 623/13.17 |
| 6,591,581 B2 | * | 7/2003 | Schmieding ........... | 53/396 |
| 2002/0007294 A1 | * | 1/2002 | Bradbury et al. ........ | 705/7 |
| 2002/0082220 A1 | * | 6/2002 | Hoemann et al. ........ | 514/21 |
| 2002/0087101 A1 | * | 7/2002 | Barrick et al. ......... | 600/587 |

OTHER PUBLICATIONS

Fogg, D. M., "Flas pans; survey process; sterilizing endoscopes; equipment rental; surgical zippers; abbreviations; floor cleaning," May 2000, Association of Operating Room Nurses, AORN Journal, pp. 1061-1064.*

Tomford, W. W., "Bone allografts: Past, present and future," 2000, Cell and Tissue Banking, pp. 105-109.*

* cited by examiner

*Primary Examiner*—Gerald J. O'Connor
*Assistant Examiner*—Lena Najarian
(74) *Attorney, Agent, or Firm*—Dickstein Shapiro LLP

(57) ABSTRACT

A method for selling a product and all phases of service and support to a customer for optimal use of the product includes customizing a product for a surgical allograft procedure to be performed and providing the customized product and services as an integrated turnkey package to a medical provider. The products include bone and soft tissue allografts for all types of orthopedic reconstructive procedures and a loan of the associated instrumentation. The service portion of the package includes training support on use of the instruments, training of operating room personnel, technical and customer support both before the performance of the procedure and on-site support. After completion of the surgical procedure, the service provider arranges for the return of the loaned instrumentation.

7 Claims, 1 Drawing Sheet

US 7,548,865 B2

METHOD OF SELLING PROCEDURE SPECIFIC ALLOGRAFTS AND ASSOCIATED INSTRUMENTATION

This application claims the benefit of U.S. Provisional Application Ser. No. 60/241,764, filed Oct. 20, 2000.

BACKGROUND OF THE INVENTION

1. Field of the Invention

The present invention relates to a business method of selling a surgical product and necessary instrumentation for using the product together with a service package including training for using the product and associated instruments, customer service and technical support.

2. Brief Description of the Related Art

In preparing to perform a surgical procedure requiring a bone or soft tissue allograft, it was heretofore necessary for the surgeon, hospital, or medical center performing the procedure to make arrangements with a tissue bank for the delivery of the allograft within the appropriate time window prior to the surgery. If the surgeon or medical facility does not already own the necessary instrumentation to be used to perform the procedure, then separate arrangements must also be made to purchase, lease or borrow the appropriate instruments through a provider or another medical facility. Additionally, the surgeon performing the procedure may need training if he or she is unfamiliar with the procedure or needs a "refresher" course, thus requiring additional arrangements to be made with yet another entity who can provide the training. Thus, the administrative preparation for the surgical procedure can become quite complex and time consuming for the medical provider.

SUMMARY OF THE INVENTION

To address the disadvantages encountered in the prior art, it is an object of the present invention to streamline the pre-operative process for the medical provider to thereby enable the medical provider to focus on providing medical care to its patients.

It is also an object of the present invention to provide a comprehensive turnkey service to a medical provider as support for the performing of a surgical allograft procedure.

It is a further object of the present invention to provide a business method of selling a surgical product along with a loan of the necessary instrumentation for using the product, together with a service package including training on using the product and associated instruments, customer service and technical support.

It is a still further object of the present invention to maintain an ongoing business relationship with a source provider of the surgical product as part of the business method to facilitate providing the turnkey service to the medical provider.

The present invention is a method for selling a product and all phases of service and support to a customer for optimal use of the product. Moreover, the product itself is specially designed according to the conditions and needs of the procedure to be performed.

In particular, the products include bone and soft tissue allografts for all types of orthopedic reconstructive procedures and a loan of the associated instrumentation. The service portion of the package includes training support on use of the instruments, training of operating room personnel, technical in-service and customer support.

When the surgeon determines that allograft surgery is necessary, upon compiling the necessary medical data, the surgeon or hospital places the order for the allograft through the service provider, who then makes the appropriate arrangements to coordinate the delivery of the allograft from a tissue bank with the assembly and delivery of a customized set of instrumentation for the specific procedure. The service provider also arranges for any training which may be necessary for the surgeon, provides for the presence of a service representative in the operating room to assist the surgeon during the procedure, and arranges for the return of the loaned instrumentation after the procedure.

Other features and advantages of the present invention will become apparent from the following description of the invention which refers to the accompanying drawings.

DETAILED DESCRIPTION OF EMBODIMENTS OF THE INVENTION

Figure 1:
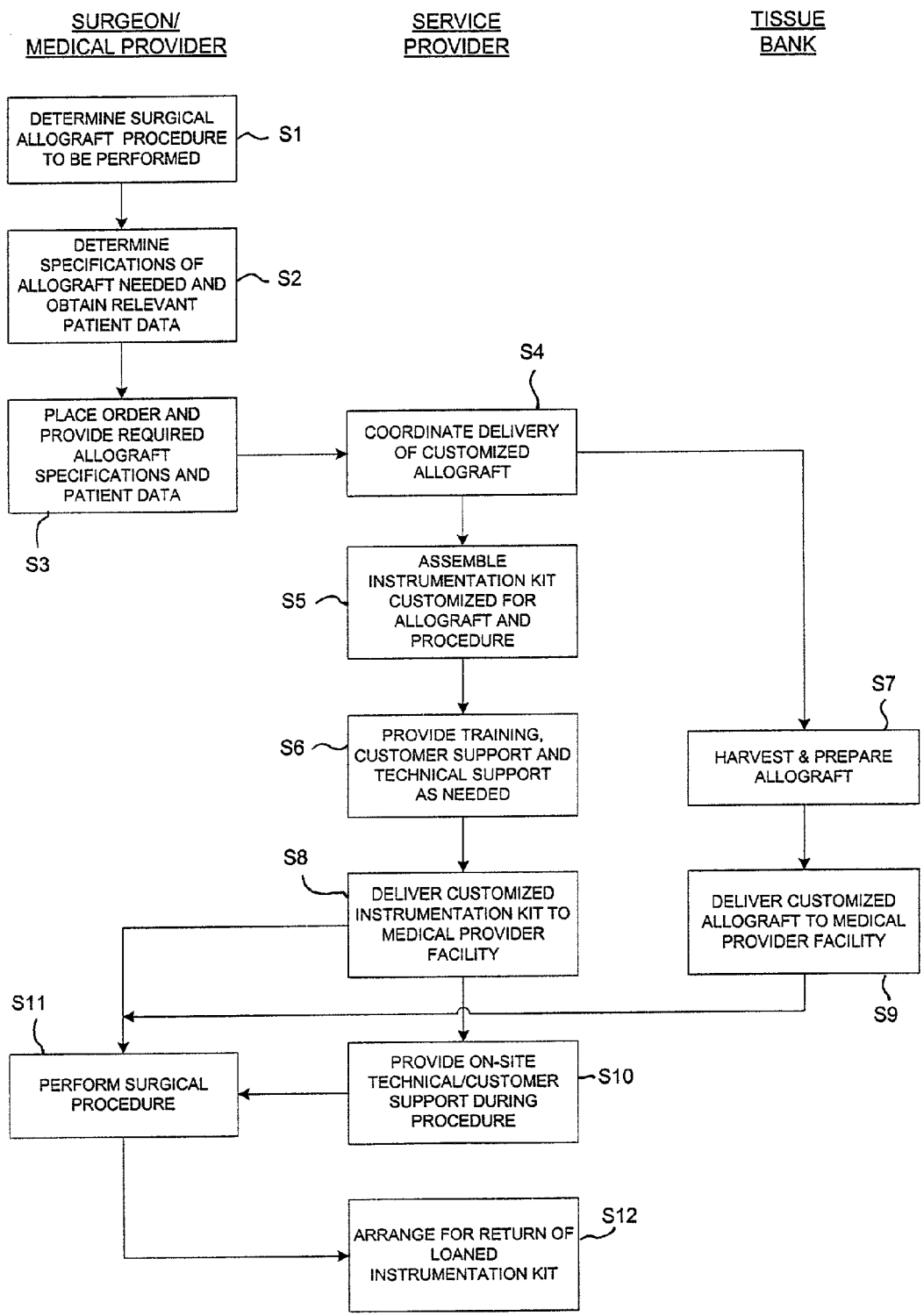
FIG. 1 is a flowchart illustrating the method in accordance with the present invention.

The present invention is a business method of providing an integrated product and service package for orthopedic surgery practitioners, and is illustrated in the flow chart shown in FIG. 1. Specifically, the inventive method serves as a single source provider of bone and soft tissue allografts for reconstructive surgical procedures, associated instrumentation and peripheral materials to perform the specified surgical procedure, and all levels of training, service and support in the use of the products.

Upon determination between an orthopedic surgeon and a patient that a reconstructive procedure is to be performed (step S1), the practitioner determines the specifications for the grafts needed for the procedure, and then collects relevant records and information useful for obtaining a customized allograft for the procedure (step S2). Such data to be collected may include the patient's blood type, the identification of any antibiotic or other allergies suffered by the patient, the dimensions of the grafts needed, X-rays and/or other pre-operative documentation.

The surgeon or the medical facility then places an order with the service provider which practices the business method of the present invention, and provides the obtained medical data to the service provider (step S3). The medical provider can order the allograft together with a loan of the associated instrumentation for performing the allograft procedure, or, if the medical provider already owns the appropriate instrumentation, the allograft only.

As part of the overhead structure of the business method arrangement, the service provider maintains an ongoing relationship with one or more tissue banks, in which the service provider provides instrumentation and training to the tissue bank personnel as needed for harvesting the allografts in accordance with the processing techniques and specifications for the procedures indicated by the customer. Such relationship is mutually beneficial to both the service provider and the tissue bank since the tissue bank personnel receives updated equipment and ongoing opportunities for training in the use of the instrumentation and harvesting techniques, while the service provider is assured of a reliable source of size specific allografts prepared specifically for the surgical procedures to be performed and the instrumentation to be used by the customers.

In accordance with the business arrangement between the tissue bank(s) and the service provider, when an order is received from a medical provider customer, the service provider contacts the tissue bank to arrange for a graft to be harvested in accordance with the specifications and indications provided by the medical provider, and to schedule the delivery of the allograft within a designated time frame prior to the scheduled surgery (step S4).

The allografts are harvested at the tissue bank from donors under standard operating room sterile techniques and are subjected to extensive tests and studies to guard against the possibility of transmission of HIV, hepatitis, and other infections and to avoid problems with recipient immune sensitization and antibiotic sensitivities.

The allografts are preferably non-irradiated and can be preserved by any method, including fresh preserved, fresh freezing, cryopreservation, freeze-drying, and decellurization. Furthermore, the allografts are customized to the specifications and conditions of the patient and the procedure. For example, the dimensions of the graft can be specifically obtained to accommodate requested dimensions (diameter, length, width and/or thickness of the grafts), or if a patient is known to be sensitive to certain antibiotics normally used in the processing of the allografts, the allografts can be prepared without the use of antibiotics.

Examples of the types of grafts which may be supplied in accordance with the present method include size specific osteochondral cores; cancellous tunnel plugs; femoral and tibial meniscus allografts (frozen and cryopreserverd) including femoral menisci with bone blocks and tibial plateau with meniscus; proximal tibial and distal femoral bone wedges; cortical cervical rings; fresh osteochondral allografts such as femoral hemi-condyles, whole distal femurs, trochleas, talus, and patellas; and anterior cruciate and posterior cruciate ligament reconstruction allografts (frozen and cryopreserved) including Achilles tendons with bone blocks, quadriceps tendons with bone blocks, hamstrings (semi-tendinosus, gracilis), anterior and posterior tibialis tendons, bone-tendon-bone tendons, and hand and foot flexor and extensor tendons.

For each order in which a loan of the corresponding instrumentation for the selected allograft has been requested, a customized instrumentation kit is assembled to include the appropriate precision instruments and fixation elements, such as fixation plates, interference screws, etc., taking into account the type and size of the requested allograft, for optimally implanting the graft (step S5). Preferably, the instruments loaned to the surgeon or medical facility for the operation are owned by the service provider. Alternatively, the service provider may arrange for the instruments to be sent to the surgeon or medical facility from another provider.

The service provider confirms the delivery date of the grafts and works with the patient's medical team to establish a system of training, if necessary, to take place either at the surgeon's facilities and/or an outside training facility, which may be operated by the service provider or a third party (step S6).

In accordance with the schedule determined between the service provider and the surgeon, the graft specific instrumentation, fixation aids, and associated materials are delivered to the operating location for in-service with the operating room staff and for sterilization (if not already provided in a sterilized state) (step S8). Meanwhile, at the tissue bank, the allograft is harvested according to the specifications indicated by the medical provider (step S7), and then packaged and shipped to the surgeon or hospital in a cooled packaging, if necessary (step S9). The delivery of the graft is coordinated to be delivered to the designated medical facility with a simultaneous or temporally proximal delivery of the graft specific instrumentation and related materials needed to perform the implantation. Preferably, the procedure specific allograft is shipped from the tissue bank by overnight delivery to the operating location 1-2 days in advance of the surgery, to arrive no later than the day of the operation.

If the operation is unforeseeably postponed or otherwise does not take place withing a day or two of the date the allograft is received from the tissue bank, the surgeon should at least keep in mind that fresh grafts such as precut osteochondral cores must be used within 14 days to maintain live cells in the allograft. With frozen or cryopreserved allografts, however, more flexibility may be afforded for the usable time frame of the graft, provided the receiving medical provider has adequate storage facilities to appropriately maintain the viability of the graft.

Prior to and during the surgical procedure, the service provider provides technical and customer support to ensure smooth operation of the procedure and to maximize the degree of success achieved by the procedure (S6, S10). In particular, if desired by the surgeon, the service provider sends a technical service representative who is knowledgeable about the surgical procedure and the use of the instrumentation and associated materials to be present with the surgeon at the time of surgery (step S10) to provide technical support and guidance for the surgeon and the operation staff during the operation (step S11).

After the operation is completed, a representative of the provider facilitates return of the loaned instrumentation and any other non-disposable materials to the provider (step S12).

As described above, the present invention provides a turnkey system in which a service provider loans a medical provider a customized instrumentation kit as an integrated package with the allograft for a specified surgical procedure, along with training and technical support services. Since tissue banks generally do not provide the instrumentation or training needed to implant a graft harvested from their facilities and instrument companies generally do not sell allografts, the system of the present invention streamlines the pre-operative administrative preparation process for the medical provider so that the medical provider need only place an order with the service provider for all the necessary arrangements to prepare for the surgical procedure.

As a business venture, the turnkey system and method of providing the integrated product and service package described herein is profitable for the service provider by charging the medical provider a fee between about 50% to 100% above the cost of obtaining the allograft from the tissue bank. The profit collected by the service provider is based upon the rental of the instrumentation, the intra-operative support, educational training, and service coordination efforts, and not on the sale of the allograft, as such sale would likely pose ethical concerns.

However, medical facilities often cannot or will not bill for loaner fees for the instrumentation, because most insurance carriers only provide coverage for products and services received for medical care. More specifically, most insurance carriers will not reimburse a medical provider or a patient for the rental costs of instrumentation, because they are ultimately returned to the instrument provider where neither the patient nor the medical provider will derive further future benefit or use from the loaned instrumentation (unless another loaner fee is paid to the instrument provider). Thus, the fee charged for the integrated product and service package is billed to the customer as the price of the graft, while the rental of the instrumentation and associated materials are included for free as part of the package. In this manner, the entire cost of the package (obtaining the allograft at cost through the tissue bank plus the rental fee for the instrumentation) is built into the cost of the allograft. The tissue bank recovers the cost of providing the allograft from the service provider. Such cost thus represents a portion of the cost of the integrated package paid by the medical provider (or the insurance carrier) to the service provider.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A method of preparing a customized donor allograft for a predetermined surgical procedure, the method comprising:

receiving at a first business entity predetermined specifications and conditions of a patient to undergo the predetermined surgical procedure, said predetermined specifications and conditions being received from a medical provider separate from said first business entity;

the first business entity providing the predetermined specifications and conditions of the patient to a second business entity comprising a tissue bank;

the tissue bank harvesting and sizing to a specific diameter, length, width and/or thickness, at least one of a meniscal and an osteochondral donor allograft according to the predetermined specifications and conditions of the patient, and also according to the predetermined surgical procedure to be performed on the patient, as received from the first business entity, thereby creating said customized donor allograft;

the first business entity effecting delivery of the customized donor allograft from the tissue bank to the medical provider, and the first business entity delivering surgical instrumentation to the medical provider, said surgical instrumentation being selected based on the customized donor allograft and on the predetermined surgical procedure.

2. The method of claim 1, wherein the tissue bank delivers the customized donor allograft directly to the medical provider.

3. The method of claim 1, wherein the surgical instrumentation includes at least one of a fixation plate and an interference screw.

4. The method of claim 1, wherein the customized donor allograft is prepared without the use of antibiotics.

5. The method of claim 1, wherein the customized donor allograft is delivered to a medical facility at which the predetermined surgical procedure is to be performed.

6. The method of claim 1 further comprising:

the first business entity training operating personnel in the use of the surgical instrumentation to perform the predetermined surgical procedure.

7. The method of claim 1, wherein the surgical instrumentation is loaned by the first business entity to the medical provider, and wherein, at the request of the first business entity, the medical provider returns the surgical instrumentation to the first business entity after the predetermined surgical procedure is completed.

\* \* \* \* \*